US012008139B1

(12) United States Patent
Hassad

(10) Patent No.: US 12,008,139 B1
(45) Date of Patent: Jun. 11, 2024

(54) METHODS AND SYSTEMS OF FACILITATING SHARING OF MEDICAL INFORMATION ASSOCIATED WITH A PATIENT AMONG USER DEVICES

(71) Applicant: Omar Hassad, New Lenox, IL (US)

(72) Inventor: Omar Hassad, New Lenox, IL (US)

( * ) Notice: Subject to any disclaimer, the term of this patent is extended or adjusted under 35 U.S.C. 154(b) by 0 days.

(21) Appl. No.: 18/484,947

(22) Filed: Oct. 11, 2023

(51) Int. Cl.
*G16H 10/40* (2018.01)
*G06F 21/62* (2013.01)
*G16H 10/65* (2018.01)

(52) U.S. Cl.
CPC ......... *G06F 21/6245* (2013.01); *G16H 10/65* (2018.01)

(58) Field of Classification Search
CPC ............................ G06F 21/6245; G16H 10/65
USPC .............................................................. 726/1
See application file for complete search history.

(56) References Cited

U.S. PATENT DOCUMENTS

| | | | | |
|---|---|---|---|---|
| 7,558,622 | B2 | 7/2009 | Tran | |
| 10,430,556 | B2 | 10/2019 | McCauley et al. | |
| 11,297,459 | B2 | 4/2022 | Raduchel et al. | |
| 11,587,179 | B2 | 2/2023 | Pinsonneault | |
| 11,862,304 | B1 * | 1/2024 | Klein | G16H 10/40 |
| 2021/0312391 | A1 | 10/2021 | Hans | |
| 2023/0359762 | A1 * | 11/2023 | Witt | G16H 10/60 |

* cited by examiner

*Primary Examiner* — Jeffrey C Pwu
*Assistant Examiner* — Nega Woldemariam

(57) ABSTRACT

Disclosed herein is a method of facilitating sharing of medical information associated with a patient among user devices. Accordingly, the method may include transmitting a software plugin to a first user device and a second user device, transmitting indicators corresponding to a plurality of users to the first user device, receiving a communication message from the first user device, retrieving a second user information associated with a second user, analyzing the second user information and a message content based on a medical compliance guideline, determining a compliance score, retrieving a second device characteristic, transforming the communication message according to the second device characteristic, generating a transformed communication message, and transmitting the transformed communication message to the second user device.

16 Claims, 14 Drawing Sheets

METHODS AND SYSTEMS OF FACILITATING SHARING OF MEDICAL INFORMATION ASSOCIATED WITH A PATIENT AMONG USER DEVICES

FIELD OF THE INVENTION

Generally, the present disclosure relates to the field of data processing. More specifically, the present disclosure relates to methods and systems of facilitating sharing of medical information associated with a patient among user devices.

BACKGROUND OF THE INVENTION

The field of data processing is technologically important to several industries, business organizations, and/or individuals. In particular, the use of data processing is prevalent for facilitating sharing of medical information associated with a patient.

Existing techniques for facilitating the sharing of medical information associated with the patient are deficient with regard to several aspects. Specific medical care providers keep medical records in paper or electronic versions. When the medical records need to be transferred between or collected from several medical professionals (such as service providers, doctors, physicians, care providers, etc.), this process may be challenging and time-consuming. Further during emergencies, immediate conversation between the medical professionals and access to the medical records on time is crucial.

Therefore, there is a need for improved methods and systems of facilitating the sharing of medical information associated with the patient that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a method of facilitating sharing of medical information associated with a patient among user devices, in accordance with some embodiments. Accordingly, the method may include transmitting, using a communication device, a software plugin to at least one first user device associated with at least one first user and at least one second user device associated with at least one second user. Further, the software plugin may be configured to generate at least one communication user interface and establish at least one API communication between the at least one first user device and the at least one second user device through an online platform. Further, the at least one communication user interface facilitates sharing of the medical information associated with the patient. Further, the method may include transmitting, using the communication device, a plurality of indicators corresponding to a plurality of users of the online platform to the at least one first user device. Further, the plurality of users may include the at least one second user. Further, the method may include receiving, using the communication device, at least one communication message from the at least one first user device. Further, the at least one communication message may be addressed to the at least one second user. Further, the at least one communication message may include at least one message content and at least one second user identifier associated with the at least one second user. Further, the method may include retrieving, using a storage device, at least one second user information associated with the at least one second user based on the at least one second user identifier from a distributed ledger. Further, the method may include analyzing, using a processing device, the at least one second user information and the at least one message content based on at least one medical compliance guideline. Further, the method may include determining, using the processing device, a compliance score based on the analyzing. Further, the method may include retrieving, using the storage device, at least one second device characteristic corresponding to the at least one second user device. Further, the method may include transforming, using the processing device, the at least one communication message according to the at least one second device characteristic. Further, the method may include generating, using the processing device, at least one transformed communication message based on the transforming. Further, the method may include transmitting, using the communication device, the at least one transformed communication message to the at least one second user device.

Further disclosed herein is a system of facilitating sharing of medical information associated with a patient among user devices, in accordance with some embodiments. Accordingly, the system may include a communication device configured for transmitting a software plugin to at least one first user device associated with at least one first user and at least one second user device associated with at least one second user. Further, the software plugin may be configured to generate at least one communication user interface and establish at least one API communication between the at least one first user device and the at least one second user device through an online platform. Further, the at least one communication user interface facilitates sharing of the medical information associated with the patient. Further, the communication device may be configured for transmitting a plurality of indicators corresponding to a plurality of users of the online platform to the at least one first user device. Further, the plurality of users may include the at least one second user. Further, the communication device may be configured for receiving at least one communication message from the at least one first user device. Further, the at least one communication message may be addressed to the at least one second user. Further, the at least one communication message may include at least one message content and at least one second user identifier associated with the at least one second user. Further, the communication device may be configured for transmitting at least one transformed communication message to the at least one second user device. Further, the system may include a processing device communicatively coupled with the communication device. Further, the processing device may be configured for analyzing at least one second user information and the at least one message content based on at least one medical compliance guideline. Further, the processing device may be configured for determining a compliance score based on the analyzing. Further, the processing device may be configured for transforming the at least one communication message according to at least one second device characteristic. Further, the processing device may be configured for generating the at least one transformed communication message based on the transforming. Further, the system may include a storage device communicatively coupled with the processing device. Further, the storage device may be configured for retrieving the at least one second user information associated with the at least one second user based on the at least one second user identifier from a distributed ledger and retrieving the at least one second device characteristic corresponding to the at least one second user device.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAIL DESCRIPTIONS OF THE INVENTION

Figure 1:
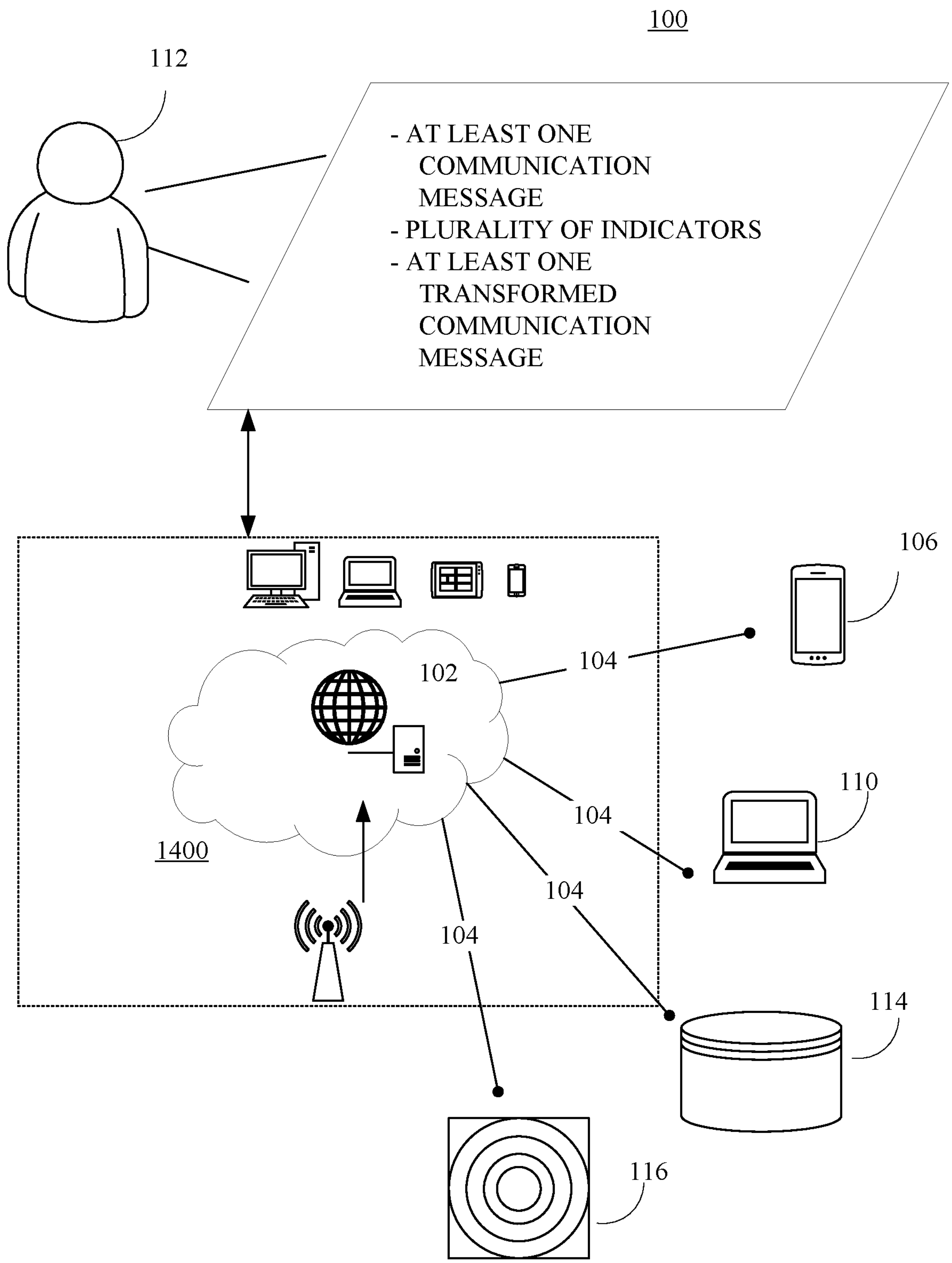
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods and systems of facilitating sharing of medical information associated with a patient among user devices, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IOT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview

The present disclosure describes methods and systems of facilitating sharing of medical information associated with a patient among user devices. Further, PAD Rx, an exemplary embodiment of the disclosed system herein, may be configured to integrate with practice management (PM) software, pharmacy management software (PMS), and electronic medical record (EMR) to facilitate two-way communication between pharmacies, doctors, healthcare providers, and clinical caregivers.

Further, the disclosed system may be HIPAA compliant. Further, both users on either end of the communication may be licensed healthcare professionals working on care for the same patient, therefore HIPAA requirements are met. The disclosed system is also fully secured. Further, users may be assigned a unique and identifying Provider ID (PID) upon initial use to help ensure that the messages are sent to the correct provider. Further, the disclosed system may be user-friendly and allow the users to securely communicate with other professionals about patient care in seconds. Further, the disclosed system may support Text, PDF, PNG, JPG, and voice formats. Further, PAD Rx integrates via API with popular PM software and EMR programs that healthcare professionals may be already using. Further, the users do not have to open a separate software application to send and receive messages.

Further, in some embodiments, the disclosed method may include a user clicking on the PAD Rx icon from the PM software, PMS, or EMR (also called an electronic health record or EHR). Further, the method may include the user typing or recording a message regarding a patient's care. Further, the method may include the user optionally attaching images or documents in PDF, PNG, or JPG format. Further, the PADRx facilitates instant message delivery to the recipient. Further, the method may include a recipient seeing a notification of the message in their PM software, PMS, or EMR program. Further, the method may include the recipient replying to the message, and attaching images or documents if necessary.

Further, in some embodiments, the disclosed system may receive one or more messages from a sender. Further, the disclosed system may be configured for automatically generating one or more responses using a machine learning model. Further, the disclosed system may be configured for transmitting the message and the one or more responses to the receiver or a second user. This way the burden on the second user to reply to the message can be reduced.

Further, in some embodiments, the disclosed system may be configured to periodically monitor an API configuration of software on the second user device of the receiver. Further, when the API configuration changes, the disclosed system may be configured to automatically (machine learning, AI, etc.) perform the transforming of the message according to a changed API configuration of the second user device. Consequently, if a vendor of a company makes updates to the software on the second user device, the communication between the sender and the receiver on the disclosed platform won't break down.

Further, in an instance, the software on the second user device may be HIPAA compliant but of lesser security. Further, in some embodiments, the disclosed system may be configured to analyze second user device characteristic associated with the second user based on a security compliance and perform any additional data protection measures (e.g. encryption, anonymization, scrambling, etc.) before transmitting the transformed message to the second user.

Further, in some embodiments, the disclosed system may be configured to analyze all communications identify trends in the message, and generate a workflow recommendation for treatment of the patient accordingly. Further, the disclosed system may be configured to transmit the workflow recommendation to one or more parties to prevent the need for such communication in the future.

This may improve the functioning of the Healthcare Management system as a whole. In other words, the disclosed system may be configured to discover problems/inefficiencies (that force users to communicate for confirmation/clarification, etc.) in the working of the medical professionals and address them.

Further, in some embodiments, the disclosed system may be configured to use machine learning to determine a criticality of the message. Further, if the criticality exceeds a certain threshold, the disclosed system may be configured to determine the ID of a personal communication device (phone, etc.) associated with the second user and transmit the message to the personal communication device.

Further, in some embodiments, if a response to the message is not received within a preset time interval, then the disclosed system may perform a remedial action. Further, the remedial action may include automatically routing the message to one or more substitute second users to increase the chances of obtaining a response. Further, the disclosed system may be configured to automatically generate possible responses using machine learning models and past communications on the disclosed system.

FIG. 1 is an illustration of an online platform 100 consistent with various embodiments of the present disclosure. By way of non-limiting example, the online platform 100 for facilitating sharing of medical information associated with a patient among user devices may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114, and sensors 116 over a communication network 104, such as, but not limited to, the Internet. Further, users of the online platform 100 may include relevant parties such as, but not limited to, end-users, administrators, service providers, service consumers and so on. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 1400.

Figure 2:
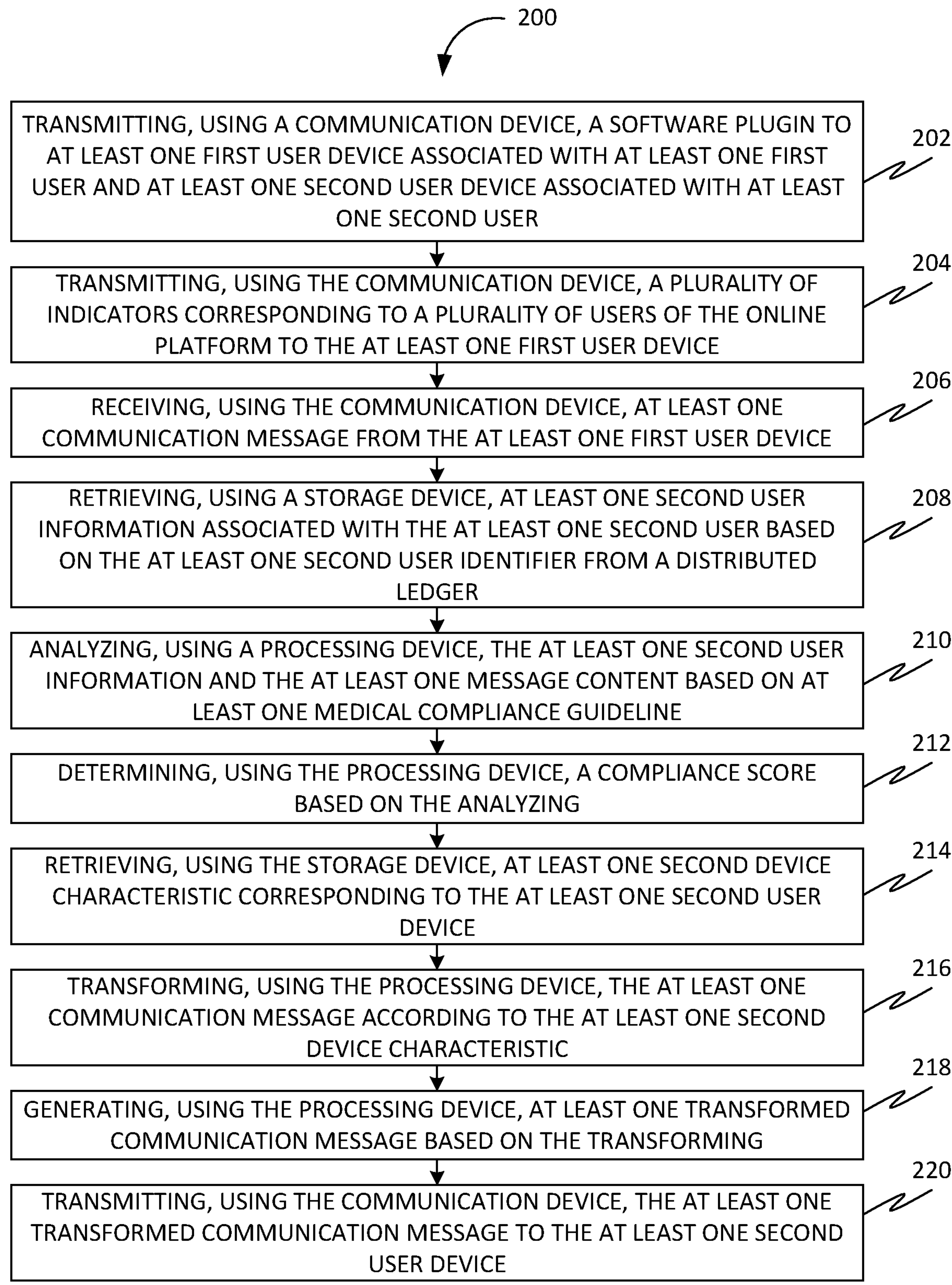
FIG. 2 is a flowchart of a method 200 of facilitating sharing of medical information associated with a patient among user devices, in accordance with some embodiments.

FIG. 2 is a flowchart of a method 200 of facilitating sharing of medical information associated with a patient among user devices, in accordance with some embodiments. Accordingly, at 202, the method 200 may include transmitting, using a communication device (such as a communication device 1102), a software plugin to at least one first user device (such as at least one first user device 1202) associated with at least one first user and at least one second user device (such as at least one second user device 1204) associated with at least one second user. Further, the software plugin may be configured to generate at least one communication user interface and establish at least one API communication between the at least one first user device and the at least one second user device through an online platform. Further, the at least one communication user interface facilitates sharing of the medical information associated with the patient. Further, at 204, the method 200 may include transmitting, using the communication device, a plurality of indicators corresponding to a plurality of users of the online platform to the at least one first user device. Further, the plurality of users may include the at least one second user. Further, at 206, the method 200 may include receiving, using the communication device, at least one communication message from the at least one first user device. Further, the at least one communication message may be addressed to the at least one second user. Further, the at least one communication message may include at least one message content and at least one second user identifier associated with the at least one second user. Further, the at least one message content may include a textual content and a graphical content. Further, in an instance, the at least one message content may include a document with an extension such as .TXT, .PDF, .PNG, .JPG, and so on. Further, at 208, the method 200 may include retrieving, using a storage device (such as a storage device 1106), at least one second user information associated with the at least one second user based on the at least one second user identifier from a distributed ledger. Further, at 210, the method 200 may include analyzing, using a processing device (such as a processing device 1104), the at least one second user information and the at least one message content based on at least one medical compliance guideline. Further, the at least one medical compliance guideline may be associated with an medical regulation act such as HIPAA. Further, at 212, the method 200 may include determining, using the processing device, a compliance score based on the analyzing. Further, at 214, the method 200 may include retrieving, using the storage device, at least one second device characteristic corresponding to the at least one second user device. Further, the at least one second device characteristic may include a software characteristic, device hardware characteristic, etc. Further, at 216, the method 200 may include transforming, using the processing device, the at least one communication message according to the at least one second device characteristic. Further, at 218, the method 200 may include generating, using the processing device, at least one transformed communication message based on the transforming. Further, at 220, the method 200 may include transmitting, using the communication device, the at least one transformed communication message to the at least one second user device.

In further embodiments, the method 200 may include storing, using the storage device, the at least one communication message and the at least one transformed communication message in the distributed ledger.

Figure 3:
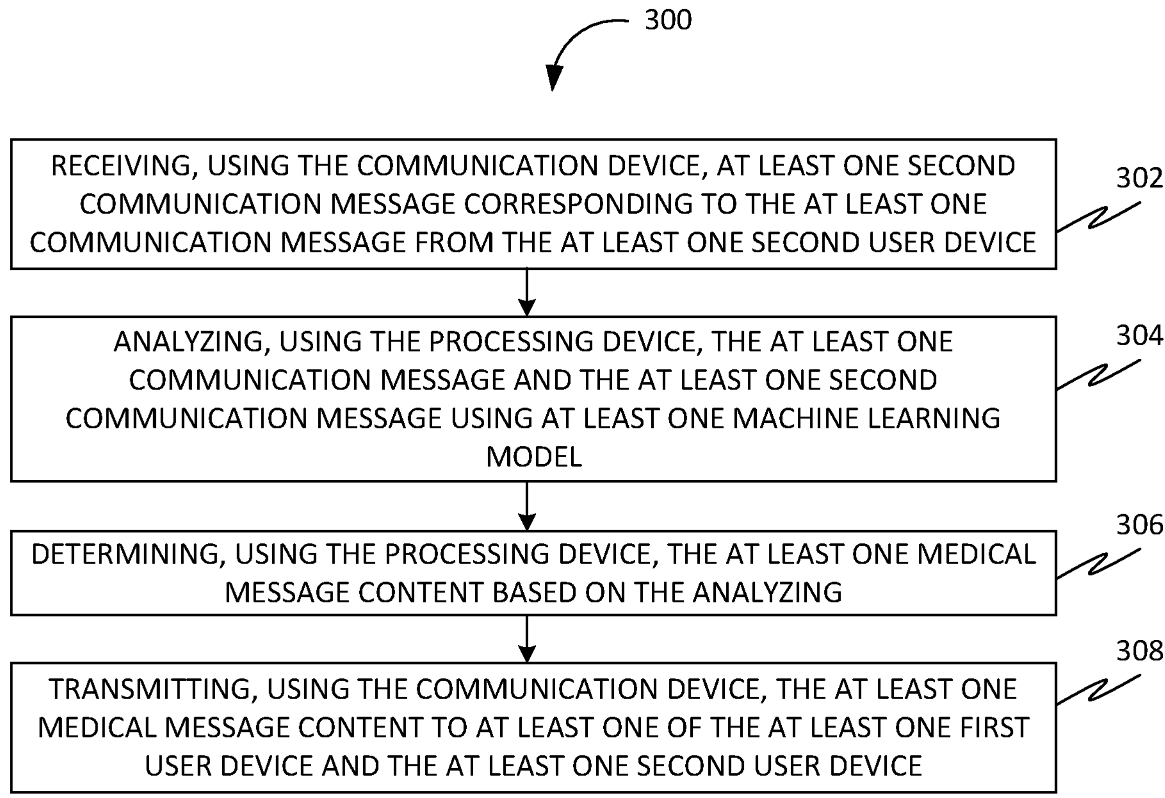
FIG. 3 is a flow chart of a method 300 of facilitating sharing of the medical information associated with the patient among user devices, in accordance with some embodiments.

FIG. 3 is a flow chart of a method 300 of facilitating sharing of the medical information associated with the patient among user devices, in accordance with some embodiments. Accordingly, at 302, the method 300 may include receiving, using the communication device, at least one second communication message corresponding to the at least one communication message from the at least one second user device. Further, the at least one second communication message may be addressed to the at least one first user. Further, the at least one second communication message may include at least one second message content and at least one first user identifier associated with the at least one first user. Further, at 304, the method 300 may include analyzing, using the processing device, the at least one communication message and the at least one second communication message using at least one machine learning model. Further, the at least one machine learning model may be trained on a dataset using at least one algorithm for identifying at least one medical message content from the at least one communication message and the at least one second communication message. Further, the at least one medical message content corresponds to a medical condition of the patient. Further, at 306, the method 300 may include determining, using the processing device, the at least one medical message content based on the analyzing. Further, at 308, the method 300 may include transmitting, using the communication device, the at least one medical message content to at least one of the at least one first user device and the at least one second user device. Further, the at least one medical message content may include a medication prescription, a medical history, a medical examination report, a blood report, an X-ray report, an X-ray film, etc.

Figure 4:
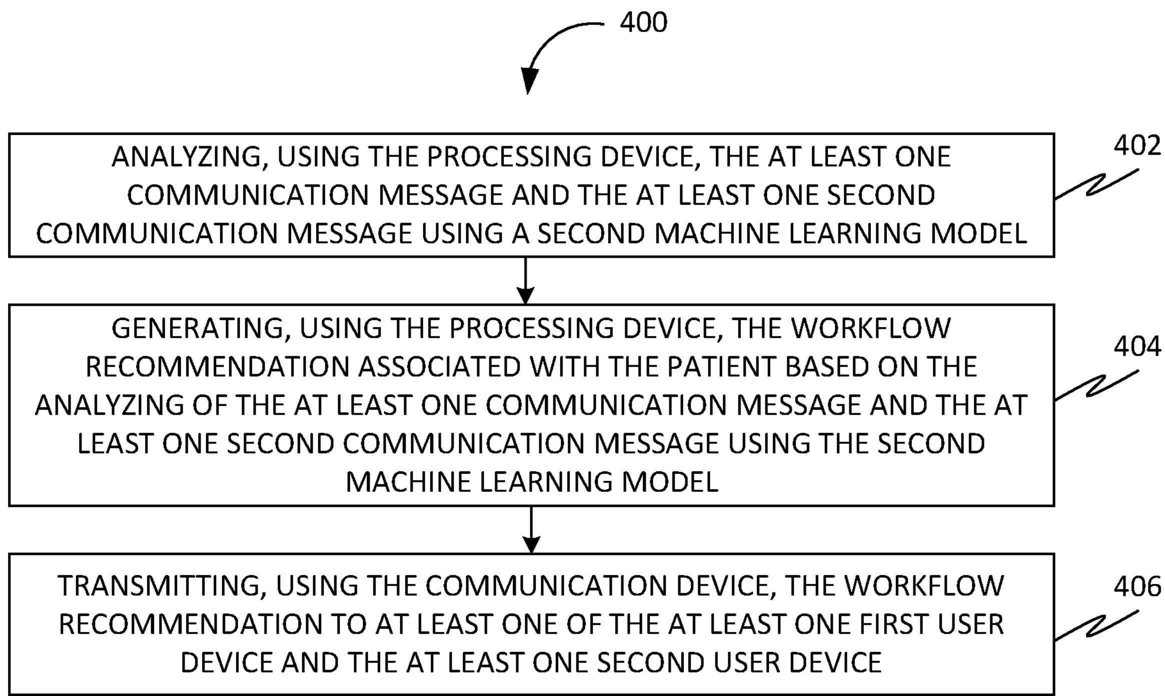
FIG. 4 is a flow chart of a method 400 of facilitating sharing of the medical information associated with the patient among user devices, in accordance with some embodiments.

FIG. 4 is a flow chart of a method 400 of facilitating sharing of the medical information associated with the patient among user devices, in accordance with some embodiments. Accordingly, at 402, the method 400 may include analyzing, using the processing device, the at least one communication message and the at least one second communication message using a second machine learning model. Further, the second machine learning model may be trained on a dataset using at least one algorithm for generating a workflow recommendation for sharing the medical information between the at least one first user and the at least one second user. Further, the second machine learning model may be configured for identifying at least one efficiency in communication between the at least one first user and the at least one second user. Further, the workflow recommendation may prevent the at least one inefficiency in future. Further, in an instance, the at least one efficiency may include a problem that may force at least one of the at least one second user and the at least one first user users to communicate for confirmation/clarification in the working of medical professionals (such as the at least one first user and the at least one second user) for treatment of the patient. Further, the workflow recommendation may include a work schedule/routine that may be followed by the at least one first user and the at least one second user. Further, in an instance, the work schedule may include at least one task to be followed by the at least one first user and the at least one second user. Further, the at least one task may include a message content that may be shared among the at least one first user and the at least one second user.

Further, at 404, the method 400 may include generating, using the processing device, the workflow recommendation associated with the patient based on the analyzing of the at least one communication message and the at least one second communication message using the second machine learning model. Further, at 406, the method 400 may include transmitting, using the communication device, the workflow recommendation to at least one of the at least one first user device and the at least one second user device.

Figure 5:
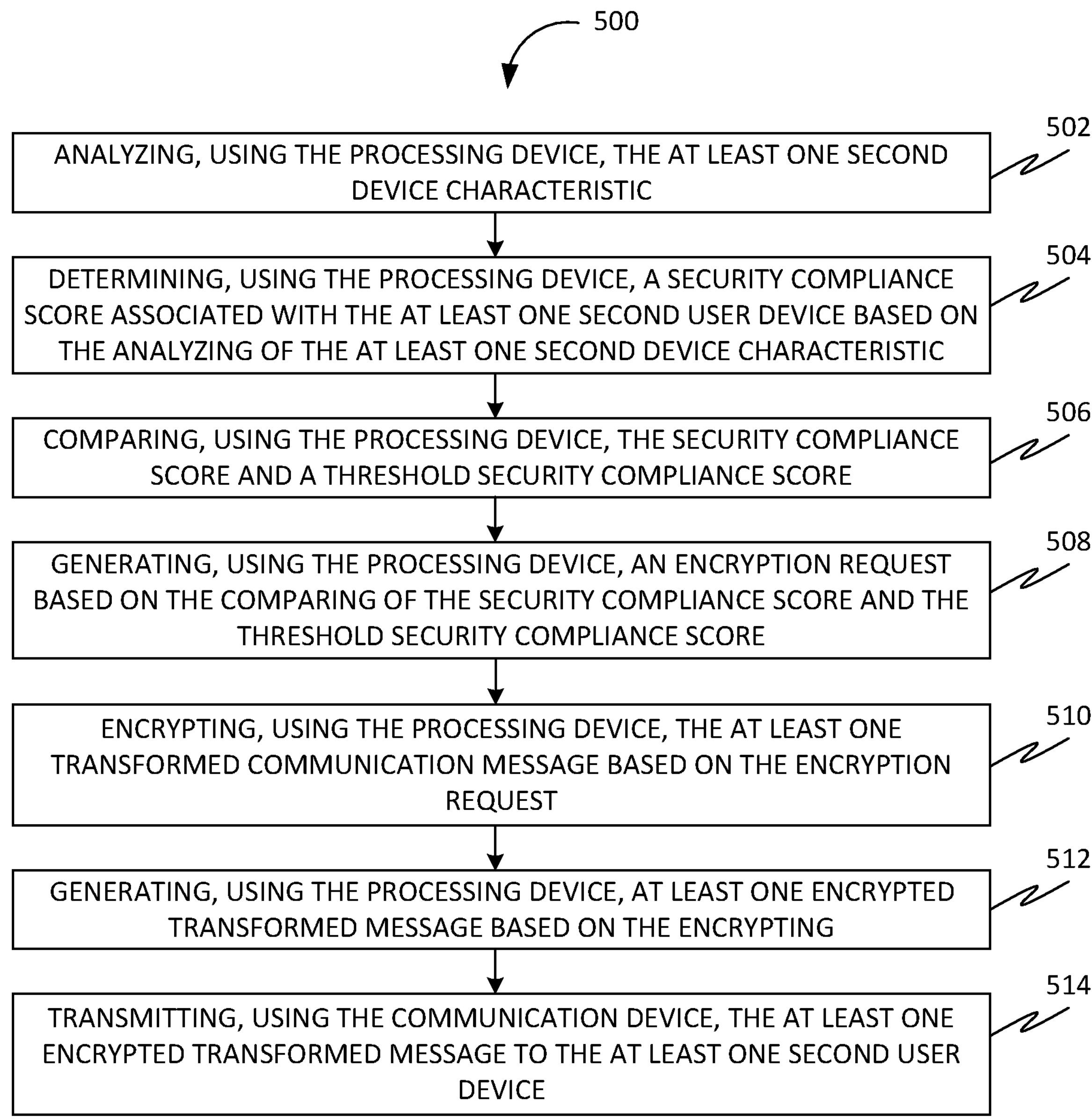
FIG. 5 is a flow chart of a method 500 of facilitating sharing of the medical information associated with the patient among user devices, in accordance with some embodiments.

FIG. 5 is a flow chart of a method 500 of facilitating sharing of the medical information associated with the patient among user devices, in accordance with some embodiments. Accordingly, at 502, the method 500 may include analyzing, using the processing device, the at least one second device characteristic. Further, at 504, the method 500 may include determining, using the processing device, a security compliance score associated with the at least one second user device based on the analyzing of the at least one second device characteristic. Further, at 506, the method 500 may include comparing, using the processing device, the security compliance score and a threshold security compliance score. Further, at 508, the method 500 may include generating, using the processing device, an encryption request based on the comparing of the security compliance score and the threshold security compliance score. Further, at 510, the method 500 may include encrypting, using the processing device, the at least one transformed communication message based on the encryption request. Further, at 512, the method 500 may include generating, using the processing device, at least one encrypted transformed message based on the encrypting. Further, at 514, the method 500 may include transmitting, using the communication device, the at least one encrypted transformed message to the at least one second user device.

Figure 6:
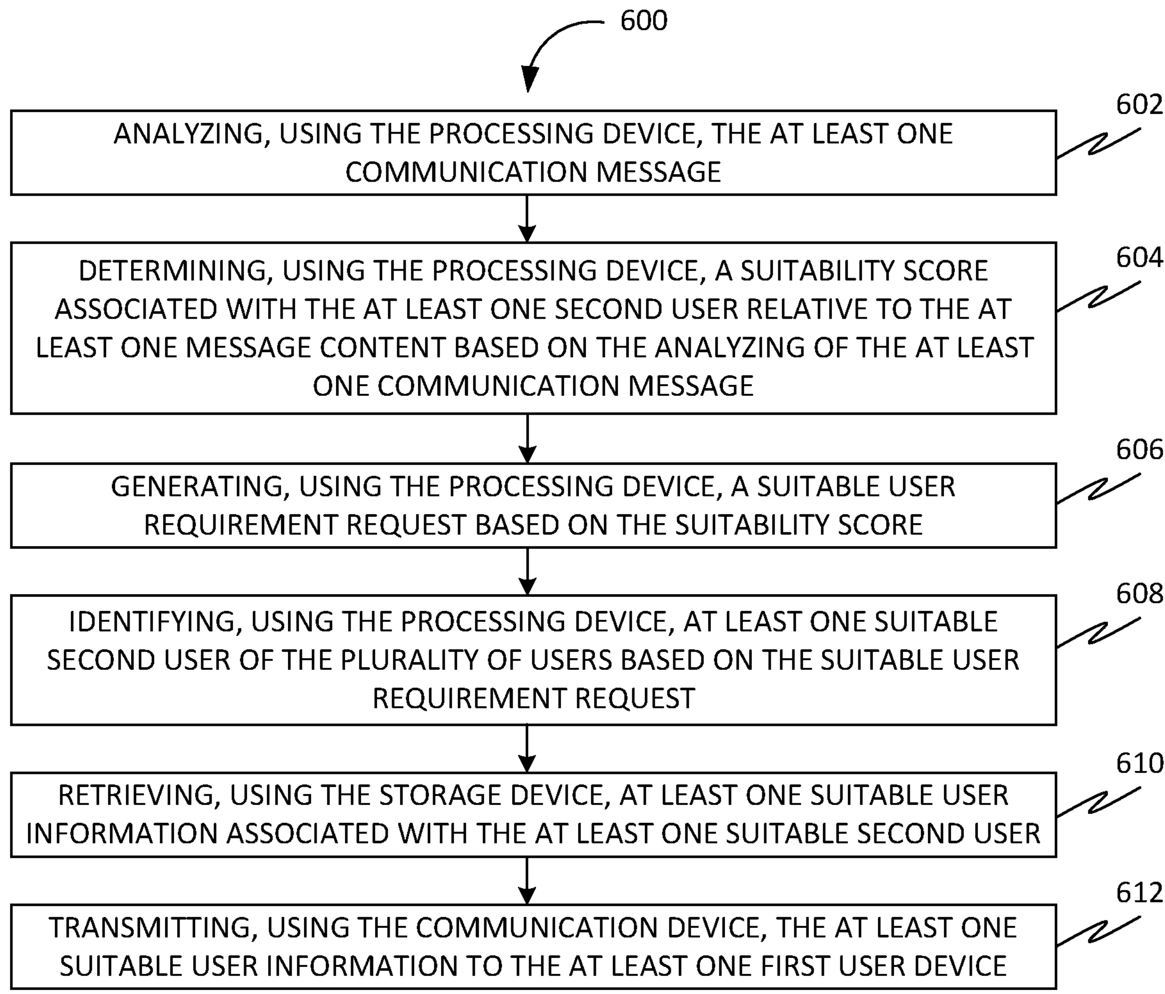
FIG. 6 is a flow chart of a method 600 of facilitating sharing of the medical information associated with the patient among user devices, in accordance with some embodiments.

FIG. 6 is a flow chart of a method 600 of facilitating sharing of the medical information associated with the patient among user devices, in accordance with some embodiments. Accordingly, at 602, the method 600 may include analyzing, using the processing device, the at least one communication message. Further, at 604, the method 600 may include determining, using the processing device, a suitability score associated with the at least one second user relative to the at least one message content based on the analyzing of the at least one communication message. Further, the suitability score represents an authorization of the at least one second user to examine the at least one message content. Further, the suitability score may indicate if the at least one second user is qualified or authorized to read or examine the at least one message content. Further, at 606, the method 600 may include generating, using the processing device, a suitable user requirement request based on the suitability score. Further, at 608, the method 600 may include identifying, using the processing device, at least one suitable second user of the plurality of users based on the suitable user requirement request. Further, the at least one suitable second user may be authorized to examine the at least one message content. Further, at 610, the method 600 may include retrieving, using the storage device, at least one suitable user information associated with the at least one suitable second user. Further, at 612, the method 600 may include transmitting, using the communication device, the at least one suitable user information to the at least one first user device.

Figure 7:
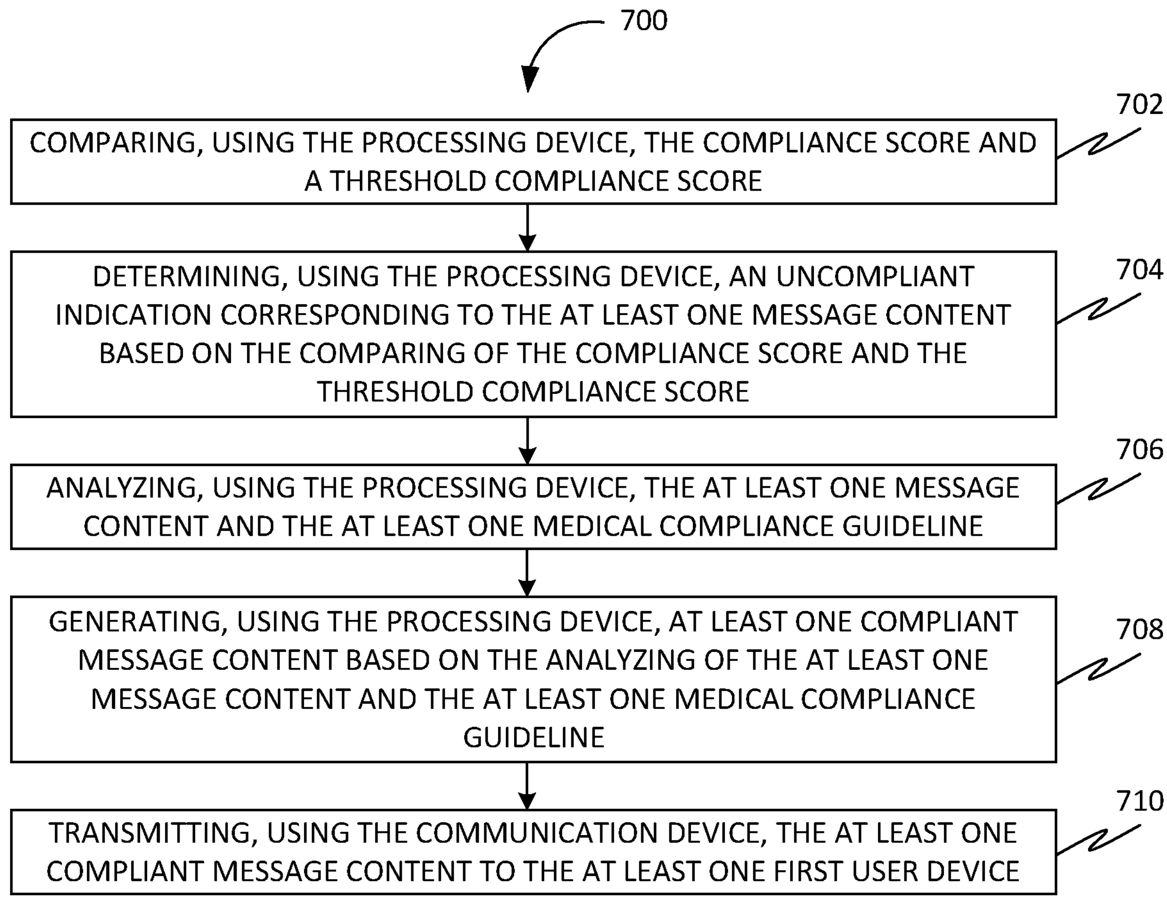
FIG. 7 is a flow chart of a method 700 of facilitating sharing of the medical information associated with the patient among user devices, in accordance with some embodiments.

FIG. 7 is a flow chart of a method 700 of facilitating sharing of the medical information associated with the patient among user devices, in accordance with some embodiments. Accordingly, at 702, the method 700 may include comparing, using the processing device, the compliance score and a threshold compliance score. Further, at 704, the method 700 may include determining, using the processing device, an uncompliant indication corresponding to the at least one message content based on the comparing of the compliance score and the threshold compliance score. Further, the uncompliant indication indicates incompliance of the at least one message content according to the at least one medical compliance guideline. Further, at 706, the method 700 may include analyzing, using the processing device, the at least one message content and the at least one medical compliance guideline. Further, at 708, the method 700 may include generating, using the processing device, at least one compliant message content based on the analyzing of the at least one message content and the at least one medical compliance guideline. Further, the at least one compliant message content may be in accordance with the at least one medical compliance guideline. Further, at 710, the method 700 may include transmitting, using the communication device, the at least one compliant message content to the at least one first user device.

Figure 8:
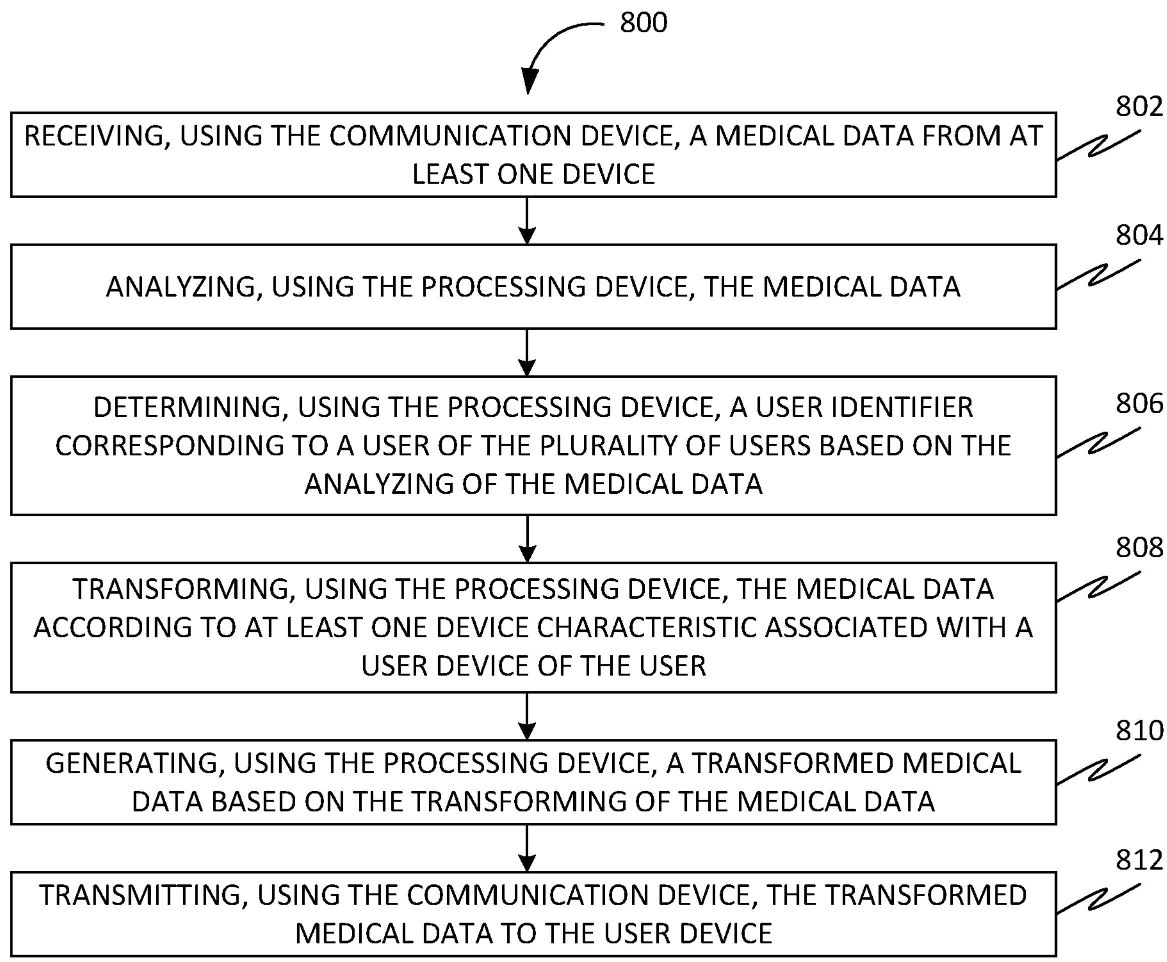
FIG. 8 is a flow chart of a method 800 of facilitating sharing of the medical information associated with the patient among user devices, in accordance with some embodiments.

FIG. 8 is a flow chart of a method 800 of facilitating sharing of the medical information associated with the patient among user devices, in accordance with some embodiments. Accordingly, at 802, the method 800 may include receiving, using the communication device, a medical data from at least one device (such as at least one device 1302). Further, the at least one device may include an imaging device, an MRI scanning device, a blood testing machine, a physiological sensor, a heart rate sensor, a blood pressure sensor, etc. Further, the at least one device may be configured for generating the medical data based on measuring at least one medical parameter of the patient. Further, at 804, the method 800 may include analyzing, using the processing device, the medical data. Further, at 806, the method 800 may include determining, using the processing device, a user identifier corresponding to a user of the plurality of users based on the analyzing of the medical data. Further, the user may be authorized to examine the medical data. Further, the user may possess at least one medical qualification degree, certificate, etc. to examine or comprehend the medical data. Further, at 808, the method 800 may include transforming, using the processing device, the medical data according to at least one device characteristic associated with a user device (such as a user device 1304) of the user. Further, the user device may include a smartphone, a tablet, a laptop, etc. Further, at 810, the method 800 may include generating, using the processing device, a transformed medical data based on the transforming of the medical data. Further, at 812, the method 800 may include transmitting, using the communication device, the transformed medical data to the user device.

Figure 9:
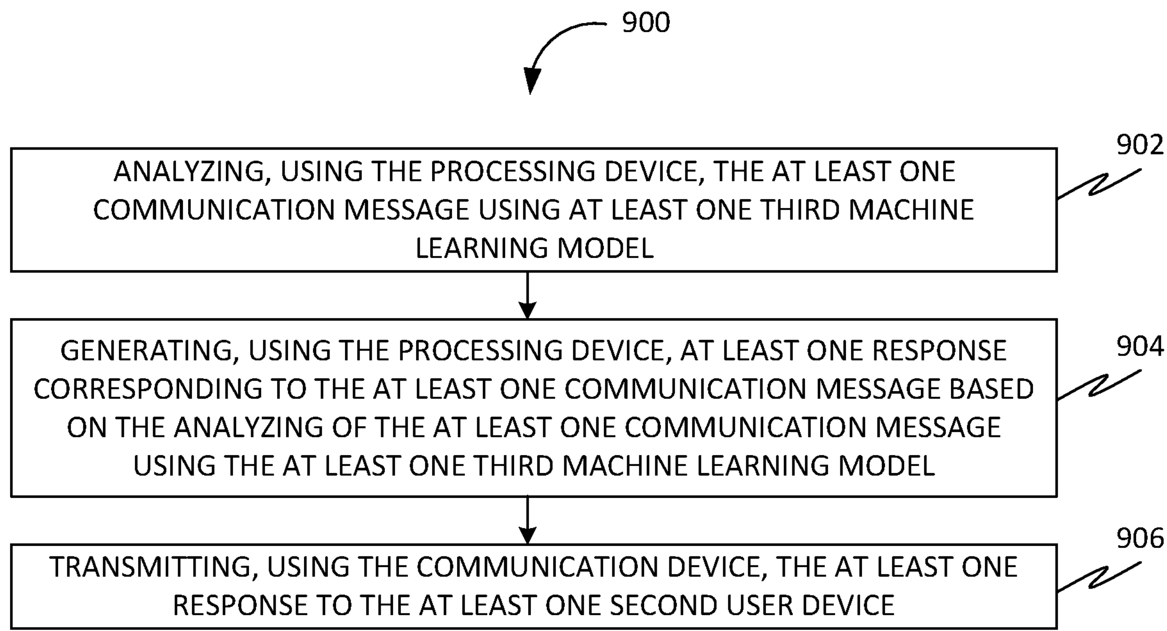
FIG. 9 is a flow chart of a method 900 of facilitating sharing of the medical information associated with the patient among user devices, in accordance with some embodiments.

FIG. 9 is a flow chart of a method 900 of facilitating sharing of the medical information associated with the patient among user devices, in accordance with some embodiments. Accordingly, at 902, the method 900 may include analyzing, using the processing device, the at least one communication message using at least one third machine learning model. Further, the at least one third machine learning model may be trained on a dataset using at least one algorithm for generating a response corresponding to the at least one communication message. Further, at 904, the method 900 may include generating, using the processing device, at least one response corresponding to the at least one communication message based on the analyzing of the at least one communication message using the at least one third machine learning model. Further, in an instance, the at least one third machine learning model may include a natural language processing model. Further, the at least one response may include a message reply to the at least one message content. Further, at 906, the method 900 may include transmitting, using the communication device, the at least one response to the at least one second user device.

Figure 10:
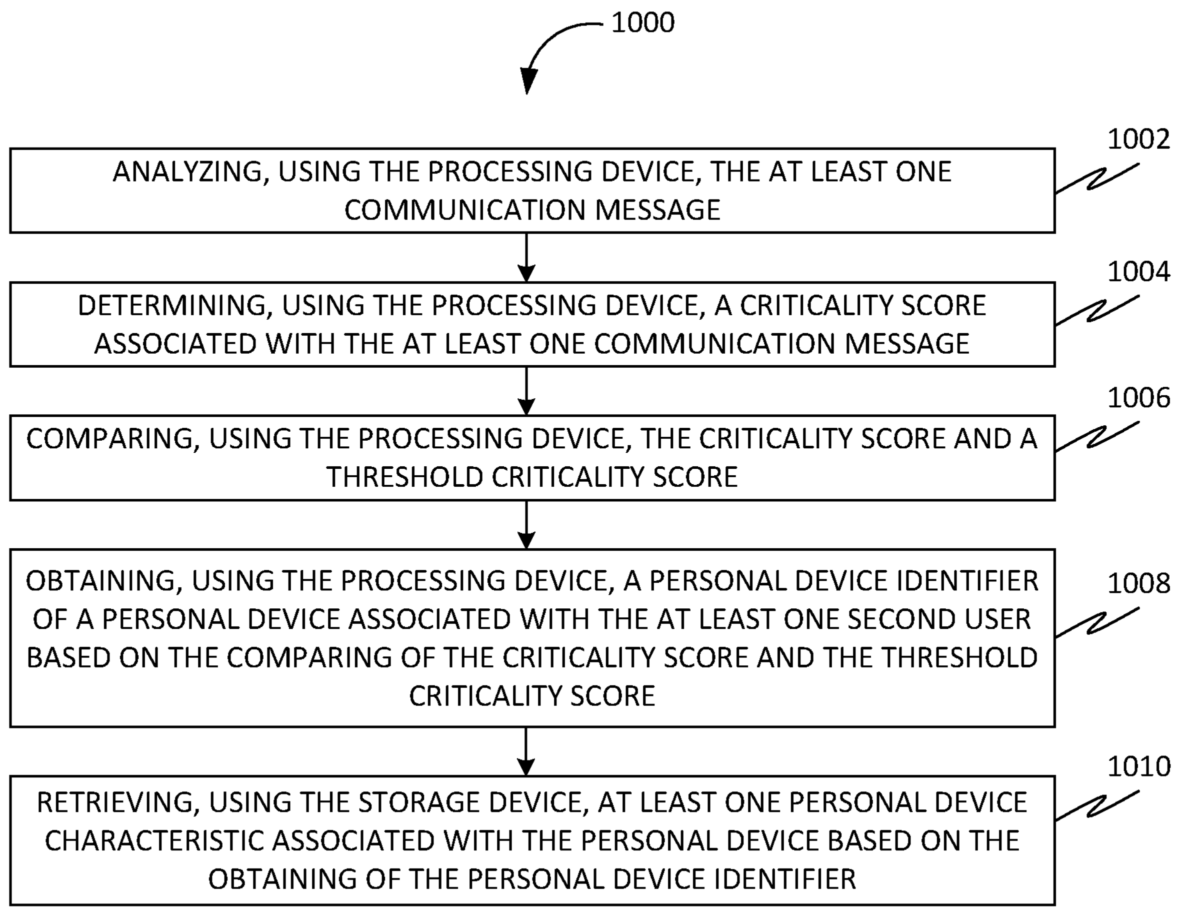
FIG. 10 is a flow chart of a method 1000 of facilitating sharing of the medical information associated with the patient among user devices, in accordance with some embodiments.

FIG. 10 is a flow chart of a method 1000 of facilitating sharing of the medical information associated with the patient among user devices, in accordance with some embodiments. Accordingly, at 1002, the method 1000 may include analyzing, using the processing device, the at least one communication message. Further, at 1004, the method 1000 may include determining, using the processing device, a criticality score associated with the at least one communication message. Further, the criticality score indicates a priority of the at least one communication message with respect to a medical condition of the patient. Further, the criticality score may represent an urgency corresponding to the medical condition of the patient. Further, the urgency may need an intervention or help by a medical professional of the at least one first user and the at least one second user for treatment of the medical condition of the patient. Further, at 1006, the method 1000 may include comparing, using the processing device, the criticality score and a threshold criticality score. Further, at 1008, the method 1000 may include obtaining, using the processing device, a personal device identifier of a personal device (such as a personal device 1306) associated with the at least one second user based on the comparing of the criticality score and the threshold criticality score. Further, the personal device may include a smartphone, a tablet, a laptop, etc. Further, at 1010, the method 1000 may include retrieving, using the storage device, at least one personal device characteristic associated with the personal device based on the obtaining of the personal device identifier. Further, the transforming may include transforming the at least one communication message according to the at least one personal device characteristic. Further, the transmitting the at least one transformed communication message may include transmitting the at least one transformed communication message to the personal device.

Figure 11:
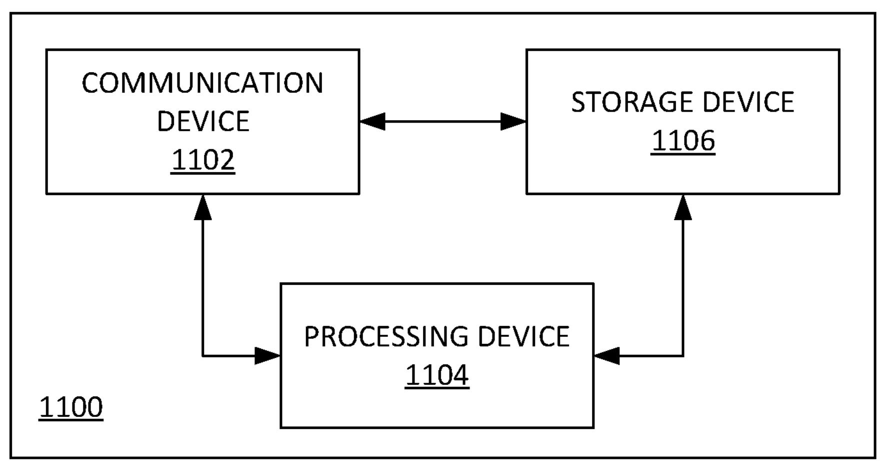
FIG. 11 is a block diagram of a system 1100 of facilitating sharing of medical information associated with a patient among user devices, in accordance with some embodiments.
Figure 12:
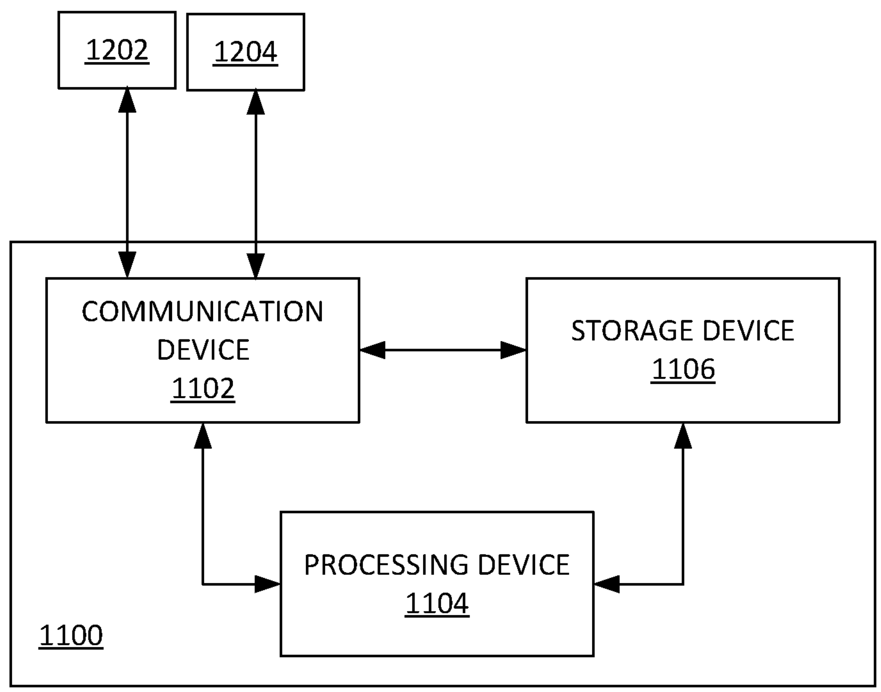
FIG. 12 is a block diagram of the system 1100 of facilitating sharing of medical information associated with the patient among user devices, in accordance with some embodiments.

FIG. 11 is a block diagram of a system 1100 of facilitating sharing of medical information associated with a patient among user devices, in accordance with some embodiments. Accordingly, the system 1100 may include a communication device 1102 configured for transmitting a software plugin to at least one first user device 1202 (as shown in FIG. 12) associated with at least one first user and at least one second user device 1204 (as shown in FIG. 12) associated with at least one second user. Further, the software plugin may be configured to generate at least one communication user interface and establish at least one API communication between the at least one first user device 1202 and the at least one second user device 1204 using an online platform. Further, the at least one communication user interface facilitates sharing of the medical information associated with the patient. Further, the communication device 1102 may be configured for transmitting a plurality of indicators corresponding to a plurality of users of the online platform to the at least one first user device 1202. Further, the plurality of users may include the at least one second user. Further, the communication device 1102 may be configured for receiving at least one communication message from the at least one first user device 1202. Further, the at least one communication message may be addressed to the at least one second user. Further, the at least one communication message may include at least one message content and at least one second user identifier associated with the at least one second user. Further, the communication device 1102 may be configured for transmitting at least one transformed communication message to the at least one second user device 1204.

Further, the system 1100 may include a processing device 1104 communicatively coupled with the communication device 1102. Further, the processing device 1104 may be configured for analyzing at least one second user information and the at least one message content based on at least one medical compliance guideline. Further, the processing device 1104 may be configured for determining a compliance score based on the analyzing. Further, the processing device 1104 may be configured for transforming the at least one communication message according to at least one second device characteristic. Further, the processing device 1104 may be configured for generating the at least one transformed communication message based on the transforming.

Further, the system 1100 may include a storage device 1106 communicatively coupled with the processing device 1104. Further, the storage device 1106 may be configured for retrieving the at least one second user information associated with the at least one second user based on the at least one second user identifier from a distributed ledger and retrieving the at least one second device characteristic corresponding to the at least one second user device 1204.

Further, in some embodiments, the storage device 1106 may be configured for storing the at least one communication message and the at least one transformed communication message in the distributed ledger.

Further, in some embodiments, the communication device 1102 may be configured for receiving at least one second communication message corresponding to the at least one communication message from the at least one second user device 1204. Further, the at least one second communication message may be addressed to the at least one first user. Further, the at least one second communication message may include at least one second message content and at least one first user identifier associated with the at least one first user. Further, the communication device 1102 may be configured for transmitting at least one medical message content to at least one of the at least one first user device 1202 and the at least one second user device 1204. Further, the processing device 1104 may be configured for analyzing the at least one communication message and the at least one second communication message using at least one machine learning model. Further, the at least one machine learning model may be trained on a dataset using at least one algorithm for identifying at least one medical message content from the at least one communication message and the at least one second communication message. Further, the at least one medical message content corresponds to a medical condition of the patient. Further, the processing device 1104 may be configured for determining the at least one medical message content based on the analyzing.

Further, in some embodiments, the processing device 1104 may be configured for analyzing the at least one communication message and the at least one second communication message using a second machine learning model. Further, the second machine learning model may be trained on a dataset using at least one algorithm for generating a workflow recommendation for sharing the medical information between the at least one first user and the at least one second user. Further, the processing device 1104 may be configured for generating the workflow recommendation associated with the patient based on the analyzing of the at least one communication message and the at least one second communication message using the second machine learning model. Further, the communication device 1102 may be configured for transmitting the workflow recommendation to at least one of the at least one first user device 1202 and the at least one second user device 1204.

Further, in some embodiments, the processing device 1104 may be configured for analyzing the at least one second device characteristic. Further, the processing device 1104 may be configured for determining a security compliance score associated with the at least one second user device 1204 based on the analyzing of the at least one second device characteristic. Further, the processing device 1104 may be configured for comparing the security compliance score and a threshold security compliance score. Further, the processing device 1104 may be configured for generating an encryption request based on the comparing of the security compliance score and the threshold security compliance score. Further, the processing device 1104 may be configured for encrypting the at least one transformed communication message based on the encryption request. Further, the processing device 1104 may be configured for generating at least one encrypted transformed message based on the encrypting. Further, the communication device 1102 may be configured for transmitting the at least one encrypted transformed message to the at least one second user device 1204.

Further, in some embodiments, the processing device 1104 may be configured for analyzing the at least one communication message. Further, the processing device 1104 may be configured for determining a suitability score associated with the at least one second user relative to the at least one message content based on the analyzing of the at least one communication message. Further, the suitability score represents an authorization of the at least one second user to examine the at least one message content. Further, the processing device 1104 may be configured for generating a suitable user requirement request based on the suitability score. Further, the processing device 1104 may be configured for identifying at least one suitable second user of the plurality of users based on the suitable user requirement request. Further, the at least one suitable second user may be authorized to examine the at least one message content. Further, the storage device 1106 may be configured for retrieving at least one suitable user information associated with the at least one suitable second user. Further, the communication device 1102 may be configured for transmitting the at least one suitable user information to the at least one first user device 1202.

Further, in some embodiments, the processing device 1104 may be configured for comparing the compliance score and a threshold compliance score. Further, the processing device 1104 may be configured for determining an uncompliant indication corresponding to the at least one message content based on the comparing of the compliance score and the threshold compliance score. Further, the uncompliant indication indicates incompliance of the at least one message content according to the at least one medical compliance guideline. Further, the processing device 1104 may be configured for analyzing the at least one message content and the at least one medical compliance guideline. Further, the processing device 1104 may be configured for generating at least one compliant message content based on the analyzing of the at least one message content and the at least one medical compliance guideline. Further, the at least one compliant message content may be in accordance with the at least one medical compliance guideline. Further, the communication device 1102 may be configured for transmitting the at least one compliant message content to the at least one first user device 1202.

Figure 13:
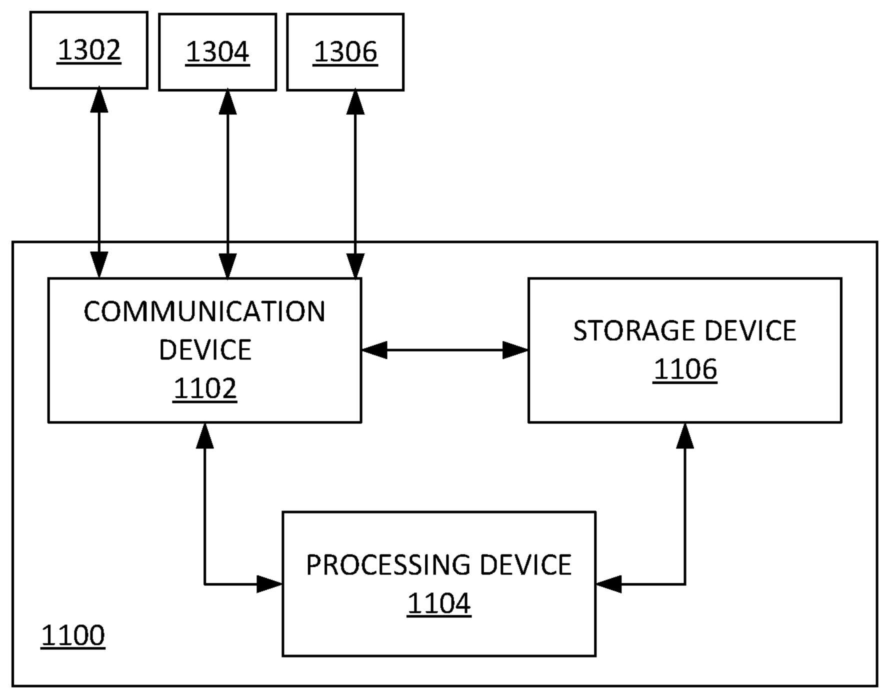
FIG. 13 is a block diagram of the system 1100 of facilitating sharing of medical information associated with the patient among user devices, in accordance with some embodiments.

Further, in some embodiments, the communication device 1102 may be configured for receiving a medical data from at least one device 1302 (as shown in FIG. 13). Further, the at least one device 1302 may be configured for generating the medical data based on measuring at least one medical parameter of the patient. Further, the communication device 1102 may be configured for transmitting a transformed medical data to a user device 1304 (as shown in FIG. 13). Further, the processing device 1104 may be configured for analyzing the medical data. Further, the processing device 1104 may be configured for determining a user identifier corresponding to a user of the plurality of users based on the analyzing of the medical data. Further, the user may be authorized to examine the medical data. Further, the processing device 1104 may be configured for transforming the medical data according to at least one device characteristic associated with the user device 1304 of the user. Further, the processing device 1104 may be configured for generating the transformed medical data based on the transforming of the medical data.

Further, in some embodiments, the processing device 1104 may be configured for analyzing the at least one communication message using at least one third machine learning model. Further, the at least one third machine learning model may be trained on a dataset using at least one algorithm for generating a response corresponding to the at least one communication message. Further, the processing device 1104 may be configured for generating at least one response corresponding to the at least one communication message based on the analyzing of the at least one communication message using the at least one third machine learning model. Further, the communication device 1102 may be configured for transmitting the at least one response to the at least one second user device 1204.

Further, in some embodiments, the processing device 1104 may be configured for analyzing the at least one communication message. Further, the processing device 1104 may be configured for determining a criticality score associated with the at least one communication message. Further, the criticality score indicates a priority of the at least one communication message with respect to a medical condition of the patient. Further, the processing device 1104 may be configured for comparing the criticality score and a threshold criticality score. Further, the processing device 1104 may be configured for obtaining a personal device identifier of a personal device 1306 (as shown in FIG. 13) associated with the at least one second user based on the comparing of the criticality score and the threshold criticality score. Further, the storage device 1106 may be configured for retrieving at least one personal device characteristic associated with the personal device 1306 based on the obtaining of the personal device identifier. Further, the transforming may include transforming the at least one communication message according to the at least one personal device characteristic. Further, the transmitting the at least one transformed communication message may include transmitting the at least one transformed communication message to the personal device 1306. Further, in some embodiments, the at least one second user device 1204 may include the personal device 1306.

FIG. 12 is a block diagram of the system 1100 of facilitating sharing of medical information associated with the patient among user devices, in accordance with some embodiments.

FIG. 13 is a block diagram of the system 1100 of facilitating sharing of medical information associated with the patient among user devices, in accordance with some embodiments.

Figure 14:
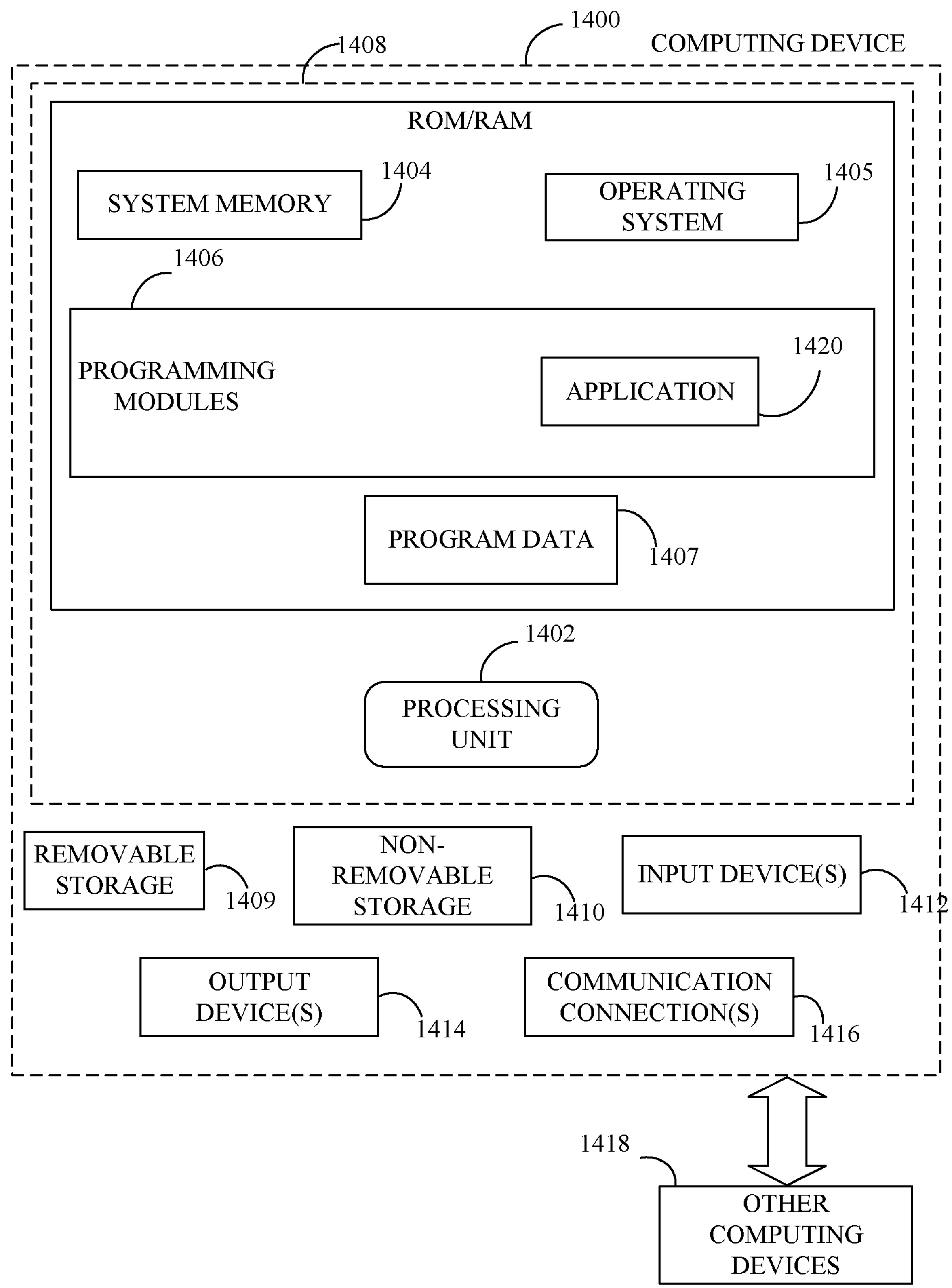
FIG. 14 is a block diagram of a computing device for implementing the methods disclosed herein, in accordance with some embodiments.

With reference to FIG. 14, a system consistent with an embodiment of the disclosure may include a computing device or cloud service, such as computing device 1400. In a basic configuration, computing device 1400 may include at least one processing unit 1402 and a system memory 1404. Depending on the configuration and type of computing device, system memory 1404 may comprise, but is not limited to, volatile (e.g. random-access memory (RAM)), non-volatile (e.g. read-only memory (ROM)), flash memory, or any combination. System memory 1404 may include operating system 1405, one or more programming modules 1406, and may include a program data 1407. Operating system 1405, for example, may be suitable for controlling computing device 1400's operation. In one embodiment, programming modules 1406 may include image-processing module, machine learning module. Furthermore, embodiments of the disclosure may be practiced in conjunction with a graphics library, other operating systems, or any other application program and is not limited to any particular application or system. This basic configuration is illustrated in FIG. 14 by those components within a dashed line 1408.

Computing device 1400 may have additional features or functionality. For example, computing device 1400 may also include additional data storage devices (removable and/or non-removable) such as, for example, magnetic disks, optical disks, or tape. Such additional storage is illustrated in FIG. 14 by a removable storage 1409 and a non-removable storage 1410. Computer storage media may include volatile and non-volatile, removable and non-removable media implemented in any method or technology for storage of information, such as computer-readable instructions, data structures, program modules, or other data. System memory 1404, removable storage 1409, and non-removable storage 1410 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1400. Any such computer storage media may be part of device 1400. Computing device 1400 may also have input device(s) 1412 such as a keyboard, a mouse, a pen, a sound input device, a touch input device, a location sensor, a camera, a biometric sensor, etc. Output device(s) 1414 such as a display, speakers, a printer, etc. may also be included. The aforementioned devices are examples and others may be used.

Computing device 1400 may also contain a communication connection 1416 that may allow device 1400 to communicate with other computing devices 1418, such as over a network in a distributed computing environment, for example, an intranet or the Internet. Communication connection 1416 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1404, including operating system 1405. While executing on processing unit 1402, programming modules 1406 (e.g., application 1420 such as a media player) may perform processes including, for example, one or more stages of methods, algorithms, systems, applications, servers, databases as described above. The aforementioned process is an example, and processing unit 1402 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

The following is claimed:

1. A method of facilitating sharing of medical information associated with a patient among user devices, the method comprising:

transmitting, using a communication device, a software plugin to at least one first user device associated with at least one first user and at least one second user device associated with at least one second user, wherein the software plugin is configured to generate at least one communication user interface and establish at least one API communication between the at least one first user device and the at least one second user device through an online platform, wherein the at least one communication user interface facilitates sharing of the medical information associated with the patient;

transmitting, using the communication device, a plurality of indicators corresponding to a plurality of users of the online platform to the at least one first user device, wherein the plurality of users comprises the at least one second user;

receiving, using the communication device, at least one communication message from the at least one first user device, wherein the at least one communication message is addressed to the at least one second user, wherein the at least one communication message comprises at least one message content and at least one second user identifier associated with the at least one second user;

retrieving, using a storage device, at least one second user information associated with the at least one second user based on the at least one second user identifier from a distributed ledger;

analyzing, using a processing device, the at least one second user information and the at least one message content based on at least one medical compliance guideline;

determining, using the processing device, a compliance score based on the analyzing;

retrieving, using the storage device, at least one second device characteristic corresponding to the at least one second user device;

transforming, using the processing device, the at least one communication message according to the at least one second device characteristic;

generating, using the processing device, at least one transformed communication message based on the transforming;

transmitting, using the communication device, the at least one transformed communication message to the at least one second user device;

storing, using the storage device, the at least one communication message and the at least one transformed communication message in the distributed ledger;

receiving, using the communication device, at least one second communication message corresponding to the at least one communication message from the at least one second user device, wherein the at least one second communication message is addressed to the at least one first user, wherein the at least one second communication message comprises at least one second message content and at least one first user identifier associated with the at least one first user;

analyzing, using the processing device, the at least one communication message and the at least one second communication message using at least one machine learning model, wherein the at least one machine learning model is trained on a dataset using at least one algorithm for identifying at least one medical message content from the at least one communication message and the at least one second communication message, wherein the at least one medical message content corresponds to a medical condition of the patient;

determining, using the processing device, the at least one medical message content based on the analyzing; and transmitting, using the communication device, the at least one medical message content to at least one of the at least one first user device and the at least one second user device.

2. The method of claim 1 further comprising:

analyzing, using the processing device, the at least one communication message and the at least one second communication message using a second machine learning model, wherein the second machine learning model is trained on a dataset using at least one algorithm for generating a workflow recommendation for sharing the medical information between the at least one first user and the at least one second user;

generating, using the processing device, the workflow recommendation associated with the patient based on the analyzing of the at least one communication message and the at least one second communication message using the second machine learning model; and transmitting, using the communication device, the workflow recommendation to at least one of the at least one first user device and the at least one second user device.

3. The method of claim 1 further comprising:

analyzing, using the processing device, the at least one second device characteristic;

determining, using the processing device, a security compliance score associated with the at least one second user device based on the analyzing of the at least one second device characteristic;

comparing, using the processing device, the security compliance score and a threshold security compliance score;

generating, using the processing device, an encryption request based on the comparing of the security compliance score and the threshold security compliance score;

encrypting, using the processing device, the at least one transformed communication message based on the encryption request;

generating, using the processing device, at least one encrypted transformed message based on the encrypting; and transmitting, using the communication device, the at least one encrypted transformed message to the at least one second user device.

4. The method of claim 1 further comprising:

analyzing, using the processing device, the at least one communication message;

determining, using the processing device, a suitability score associated with the at least one second user relative to the at least one message content based on the analyzing of the at least one communication message, wherein the suitability score represents an authorization of the at least one second user to examine the at least one message content;

generating, using the processing device, a suitable user requirement request based on the suitability score;

identifying, using the processing device, at least one suitable second user of the plurality of users based on the suitable user requirement request, wherein the at least one suitable second user is authorized to examine the at least one message content;

retrieving, using the storage device, at least one suitable user information associated with the at least one suitable second user; and transmitting, using the communication device, the at least one suitable user information to the at least one first user device.

5. The method of claim 1 further comprising:

comparing, using the processing device, the compliance score and a threshold compliance score;

determining, using the processing device, an uncompliant indication corresponding to the at least one message content based on the comparing of the compliance score and the threshold compliance score, wherein the uncompliant indication indicates incompliance of the at least one message content according to the at least one medical compliance guideline;

analyzing, using the processing device, the at least one message content and the at least one medical compliance guideline;

generating, using the processing device, at least one compliant message content based on the analyzing of the at least one message content and the at least one medical compliance guideline, wherein the at least one compliant message content is in accordance with the at least one medical compliance guideline; and transmitting, using the communication device, the at least one compliant message content to the at least one first user device.

6. The method of claim 1 further comprising:

receiving, using the communication device, a medical data from at least one device, wherein the at least one device is configured for generating the medical data based on measuring at least one medical parameter of the patient;

analyzing, using the processing device, the medical data;

determining, using the processing device, a user identifier corresponding to a user of the plurality of users based on the analyzing of the medical data, wherein the user is authorized to examine the medical data;

transforming, using the processing device, the medical data according to at least one device characteristic associated with a user device of the user;

generating, using the processing device, a transformed medical data based on the transforming of the medical data; and transmitting, using the communication device, the transformed medical data to the user device.

7. The method of claim 1 further comprising:

analyzing, using the processing device, the at least one communication message using at least one third machine learning model, wherein the at least one third machine learning model is trained on a dataset using at least one algorithm for generating a response corresponding to the at least one communication message;

generating, using the processing device, at least one response corresponding to the at least one communication message based on the analyzing of the at least one communication message using the at least one third machine learning model; and transmitting, using the communication device, the at least one response to the at least one second user device.

8. The method of claim 1 further comprising:

analyzing, using the processing device, the at least one communication message;

determining, using the processing device, a criticality score associated with the at least one communication message, wherein the criticality score indicates a priority of the at least one communication message with respect to a medical condition of the patient;

comparing, using the processing device, the criticality score and a threshold criticality score;

obtaining, using the processing device, a personal device identifier of a personal device associated with the at least one second user based on the comparing of the criticality score and the threshold criticality score; and retrieving, using the storage device, at least one personal device characteristic associated with the personal device based on the obtaining of the personal device identifier, wherein the transforming comprises transforming the at least one communication message according to the at least one personal device characteristic, wherein the transmitting the at least one transformed communication message comprises transmitting the at least one transformed communication message to the personal device.

9. A system of facilitating sharing of medical information associated with a patient among user devices, the system comprising:

a communication device configured for:

transmitting a software plugin to at least one first user device associated with at least one first user and at least one second user device associated with at least one second user, wherein the software plugin is configured to generate at least one communication user interface and establish at least one API communication between the at least one first user device and the at least one second user device through an online platform, wherein the at least one communication user interface facilitates sharing of the medical information associated with the patient;

transmitting a plurality of indicators corresponding to a plurality of users of the online platform to the at least one first user device, wherein the plurality of users comprises the at least one second user;

receiving at least one communication message from the at least one first user device, wherein the at least one communication message is addressed to the at least one second user, wherein the at least one communication message comprises at least one message content and at least one second user identifier associated with the at least one second user; and transmitting at least one transformed communication message to the at least one second user device;

a processing device communicatively coupled with the communication device, wherein the processing device is further configured for:

analyzing at least one second user information and the at least one message content based on at least one medical compliance guideline:

determining a compliance score based on the analyzing;

transforming the at least one communication message according to at least one second device characteristic; and generating the at least one transformed communication message based on the transforming; and a storage device communicatively coupled with the processing device, wherein the storage device is further configured for:

retrieving the at least one second user information associated with the at least one second user based on the at least one second user identifier from a distributed ledger; and retrieving the at least one second device characteristic corresponding to the at least one second user device;

wherein the storage device is further configured for storing the at least one communication message and the at least one transformed communication message in the distributed ledger;

wherein the communication device is configured for:

receiving at least one second communication message corresponding to the at least one communication message from the at least one second user device, wherein the at least one second communication message is addressed to the at least one first user, wherein the at least one second communication message comprises at Least one second message content and at least one first user identifier associated with the at least one first user; and transmitting at least one medical message content to at least one of the at least one first user device and the at least one second user device, wherein the processing device is further configured for:

analyzing the at least one communication message and the at least one second communication message using at least one machine learning model, wherein the at least one machine learning model is trained on a dataset using at least one algorithm for identifying at least one medical message content from the at least one communication message and the at least one second communication message, wherein the at least one medical message content corresponds to a medical condition of the patient; and determining the at least one medical message content based on the analyzing.

10. The system of claim 9, wherein the processing device is further configured for:

analyzing the at least one communication message and the at least one second communication message using a second machine learning model, wherein the second machine learning model is trained on a dataset using at least one algorithm for generating a workflow recommendation for sharing the medical information between the at least one first user and the at least one second user; and generating the workflow recommendation associated with the patient based on the analyzing of the at least one communication message and the at least one second communication message using the second machine learning model, wherein the communication device is further configured for transmitting the workflow recommendation to at least one of the at least one first user device and the at least one second user device.

11. The system of claim 9, wherein the processing device is further configured for:

analyzing the at least one second device characteristic;

determining a security compliance score associated with the at least one second user device based on the analyzing of the at least one second device characteristic;

comparing the security compliance score and a threshold security compliance score;

generating an encryption request based on the comparing of the security compliance score and the threshold security compliance score;

encrypting the at least one transformed communication message based on the encryption request; and generating at least one encrypted transformed message based on the encrypting, wherein the communication device is further configured for transmitting the at least one encrypted transformed message to the at least one second user device.

12. The system of claim 9, wherein the processing device is further configured for:

analyzing the at least one communication message;

determining a suitability score associated with the at least one second user relative to the at least one message content based on the analyzing of the at least one communication message, wherein the suitability score represents an authorization of the at least one second user to examine the at least one message content;

generating a suitable user requirement request based on the suitability score; and identifying at least one suitable second user of the plurality of users based on the suitable user requirement request, wherein the at least one suitable second user is authorized to examine the at least one message content, wherein the storage device is configured for retrieving at least one suitable user information associated with the at least one suitable second user, wherein the communication device is further configured for transmitting the at least one suitable user information to the at least one first user device.

13. The system of claim 9, wherein the processing device is further configured for:

comparing the compliance score and a threshold compliance score;

determining an uncompliant indication corresponding to the at least one message content based on the comparing of the compliance score and the threshold compliance score, wherein the uncompliant indication indicates incompliance of the at least one message content according to the at least one medical compliance guideline;

analyzing the at least one message content and the at least one medical compliance guideline; and generating at least one compliant message content based on the analyzing of the at least one message content and the at least one medical compliance guideline, wherein the at least one compliant message content is in accordance with the at least one medical compliance guideline, wherein the communication device is further configured for transmitting the at least one compliant message content to the at least one first user device.

14. The system of claim 9, wherein the communication device is further configured for:

receiving a medical data from at least one device, wherein the at least one device is configured for generating the medical data based on measuring at least one medical parameter of the patient; and transmitting a transformed medical data to a user device, wherein the processing device is further configured for:

analyzing the medical data;

determining a user identifier corresponding to a user of the plurality of users based on the analyzing of the medical data, wherein the user is authorized to examine the medical data;

transforming the medical data according to at least one device characteristic associated with the user device of the user; and generating the transformed medical data based on the transforming of the medical data.

15. The system of claim 9, wherein the processing device is further configured for:

analyzing the at least one communication message using at least one third machine learning model, wherein the at least one third machine learning model is trained on a dataset using at least one algorithm for generating a response corresponding to the at least one communication message; and generating at least one response corresponding to the at least one communication message based on the analyzing of the at least one communication message using the at least one third machine learning model, wherein the communication device is further configured for transmitting the at least one response to the at least one second user device.

16. The system of claim 9, wherein the processing device is further configured for:

analyzing the at least one communication message;

determining a criticality score associated with the at least one communication message, wherein the criticality score indicates a priority of the at least one communication message with respect to a medical condition of the patient;

comparing the criticality score and a threshold criticality score; and obtaining a personal device identifier of a personal device associated with the at least one second user based on the comparing of the criticality score and the threshold criticality score, wherein the storage device is further configured for retrieving at least one personal device characteristic associated with the personal device based on the obtaining of the personal device identifier, wherein the transforming comprises transforming the at least one communication message according to the at least one personal device characteristic, wherein the transmitting the at least one transformed communication message comprises transmitting the at least one transformed communication message to the personal device.

* * * * *